United States Patent [19]

Petrofsky et al.

[11] 4,421,336

[45] Dec. 20, 1983

[54] VEHICLE FOR THE PARALYZED

[75] Inventors: Jerrold S. Petrofsky, Beavercreek; Roger M. Glaser, Dayton, both of Ohio

[73] Assignee: Wright State University, Dayton, Ohio

[21] Appl. No.: 417,938

[22] Filed: Sep. 14, 1982

[51] Int. Cl.$^3$ .......................... A61G 5/02; B62M 1/04
[52] U.S. Cl. ........................................ 280/252; 3/1.1; 74/105; 74/128; 128/421; 180/6.5; 280/242 WC; 297/DIG. 4
[58] Field of Search ............. 280/252, 242 WC, 7.1 J, 280/289 WC, 249; 180/6.5, DIG. 3; 297/DIG. 4; 74/128, 105; 128/25 R, 80 R, 421, 422, 423 W; 3/1.1

[56] References Cited

U.S. PATENT DOCUMENTS

| | | | |
|---|---|---|---|
| 3,374,845 | 3/1968 | Selwyn | 180/6.5 |
| 3,387,147 | 6/1968 | Radwan | 128/422 X |
| 3,730,174 | 5/1973 | Madison | 128/25 R |
| 3,817,254 | 6/1974 | Maurer | 128/421 |
| 3,911,910 | 10/1975 | Oesau | 128/82.1 |
| 3,930,495 | 1/1976 | Marino, Jr. | 128/25 R |
| 3,991,749 | 11/1976 | Zent | 128/25 R |
| 4,071,033 | 1/1978 | Nawracaj et al. | 128/420 A |
| 4,158,196 | 6/1979 | Crawford, Jr. | 180/6.5 X |
| 4,177,819 | 12/1979 | Kofsky et al. | 128/422 |
| 4,284,157 | 8/1981 | Lay | 180/65 R |
| 4,351,406 | 9/1982 | Lay | 180/65 R |

OTHER PUBLICATIONS

Microprocessor Controlled Stimulation in Paralyzed Muscle, Jerrold S. Petrofsky & Chandler A. Phillips, IEEE NAECON Record (1979) pp. 198–210.
Control of the Recruitment and Firing Frequencies of Motor Units in Electrically Stimulated Muscles in the Cat, Petrofsky, Med. Biol. Eng. & Comput., 1978, 16, 302, 208.
Walking Away from Paralysis, Denise Grady, Discover Magazine, May, 1981, pp. 26–28 and 30.

Primary Examiner—Joseph F. Peters, Jr.
Assistant Examiner—Mitchell J. Hill
Attorney, Agent, or Firm—Biebel, French & Nauman

[57] ABSTRACT

A vehicle for transporting a paralyzed person includes a support frame for carrying the person, a plurality of wheels for carrying the support frame, and foot supports movably connected to the support frame for supporting the feet of the person. A drive system connected between the foot supports and at least one of the wheels drives the vehicle in response to movement of the legs of the person. A plurality of stimulation signals are generated and applied to a plurality of electrodes attached to the skin of the person for causing driving movement of the legs. Controls for selectively actuating the signal generator and for controlling the speed of the vehicle are provided.

14 Claims, 16 Drawing Figures

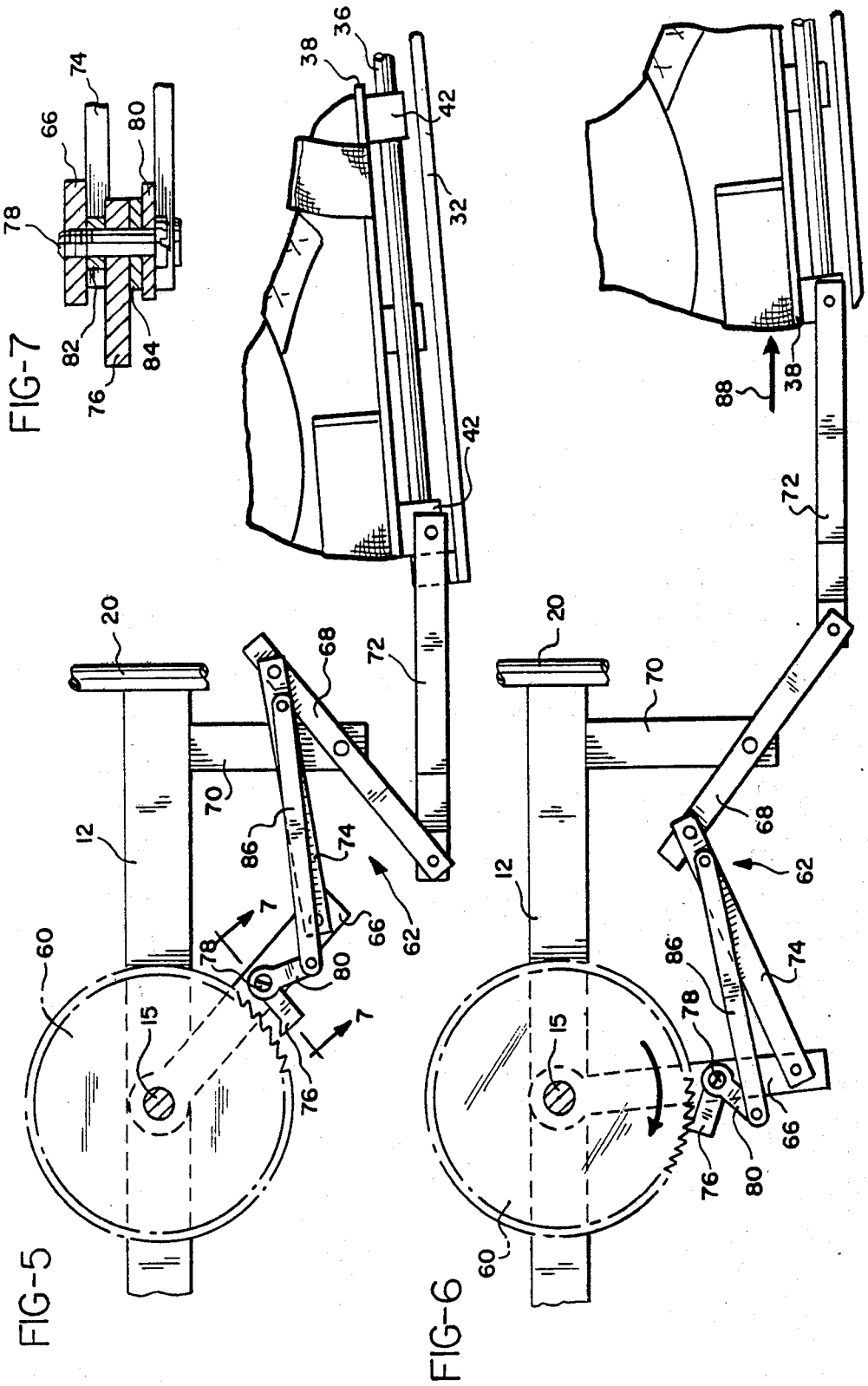

VEHICLE FOR THE PARALYZED

BACKGROUND OF THE INVENTION

The present invention relates to a vehicle for transporting a paralyzed person, and more particularly, to such a vehicle that is adapted to be driven by action of the legs of the occupant thereof.

Paralyzed individuals frequently suffer from seemingly unrelated health problems that arise as a consequence of their paralysis. For example, in the case of paraplegics, decreased physical activity due to non-use of the muscles of the lower body can often lead to various problems such as poor circulation, cardiovascular disease, and the loss of calcium from bones, which then become vulnerable to fractures.

Additionally, such individuals are faced with problems of limited mobility. While motorized wheel chairs are available, many paraplegics use manual wheel chairs, powering them by rotating the large wheels of the chair with their arms. This form of locomotion is quite stressful, however, due to the use of the relatively small and weak upper body musculature.

As is disclosed in Petrofsky et al U.S. patent application Ser. No. 417,934, filed on even date herewith, it has been discovered that in many cases of lower limb paralysis, it is possible to use electrical stimulation to cause the muscles of the paralyzed limbs to operate in controlled fashion. In most cases of lower limb paralysis, the motoneurons from the spinal cord to the skeletal muscles of the legs, as well as the muscles themselves, are functional. Reasons for the paralysis are usually due to loss of neuronal connections or function between the brain and the motoneurons which leave the spinal cord. If the motoneurons or the paralyzed muscles are stimulated directly by an electrical stimulator, muscular contraction will occur.

It would appear from this discovery that in the case of many paralyzed individuals, the health problems noted above could be reduced or eliminated by exercising the muscles of the lower body by electrical stimulation.

What is needed, therefore, is a vehicle that can be propelled by movement of the legs of a paralyzed vehicle occupant through electrical stimulation. In addition to achieving for such a person the health benefits discussed above, such a vehicle would provide at the said time for increased mobility, as well as a source of enjoyable recreational activity.

SUMMARY OF THE INVENTION

A vehicle for transporting a paralyzed person includes a support frame for carrying the person and a plurality of wheels for carrying the support frame. Limb support means connected to the support frame supports a limb of the person, and drive means connected between the limb support means and at least one of the wheels drives the vehicle in response to movement of the limb. A stimulation signal is generated, and stimulation means responsive to the stimulation signal causes driving movement of the limb. Control means are provided for selectively actuating the stimulation signal generator.

The limb support means may include means for supporting the feet of the person, the feet supporting means being movable in response to driving movement of the legs of the person.

The stimulation means may include a plurality of sets of electrodes constructed for attachment to the skin of the person, at least one of the sets being attached along each of the legs. The electrodes are responsive to a pair of stimulation signals, which comprises alternately generated pulses.

The feet support means may include a pair of pedals opposedly mounted to a rotatable crank, the driving movement of the legs of the person causing rotation of the crank by the pedals whereby forward rotation of the crank drives the vehicle in a forward direction.

The stimulation means may include at least four sets of electrodes. Sets are attached for stimulation of the quadriceps muscles of the right and left legs, and for stimulation of the right and left illiac muscles. A sensing means is provided for generating a sensing signal corresponding to forward rotation of the crank, the signal defining position angles of rotation. The control means is operative in response to the sensing signal to apply a pair of the stimulation signals to each of the electrode sets in a sequence to cause the legs of the person to rotate the crank.

Accordingly, it is an object of the present invention to provide a vehicle that may be propelled by the electrical stimulation of paralyzed limbs of the vehicle occupant; to provide such a vehicle that can obtain for the user various health benefits derived from use of the paralyzed musculature; to provide such a vehicle that achieves for the user increased mobility; and to provide such a vehicle that presents the paralyzed user with an enjoyable recreational activity.

Other objects and advantages of the present invention will be apparent from the following description, the accompanying drawings, and the appended claims.

BRIEF DESCRIPTION OF THE DRAWINGS

FIG. 5 is an elevational view showing in detail the drive system and its operation;

FIG. 6 is a view similar to FIG. 5 showing further the operation of the drive system;

FIG. 7 is a view taken generally along line 7—7 in FIG. 5;

DETAILED DESCRIPTION OF THE PREFERRED EMBODIMENTS

Figure 1:
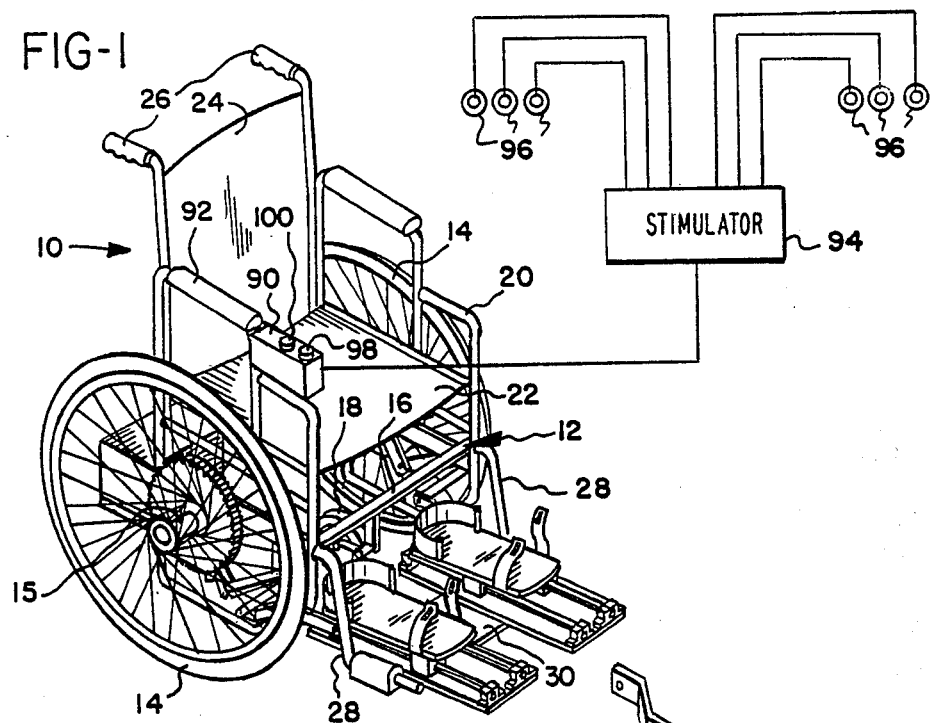
FIG. 1 is a perspective view showing a wheelchair as one embodiment of the present invention, along with a schematic representation of a circuit for providing electrical stimulation to the legs of a paralyzed chair occupant.

Referring now to FIG. 1, one species of vehicle in accordance with the present invention is illustrated generally as wheelchair 10. Included in wheelchair 10 is a chassis 12 to which is rotatably mounted a pair of relatively large side wheels 14, each on one of a pair of axles 15. The chassis 12 includes cross member 16, having pivotally mounted thereto a smaller front wheel 18. To the chassis 12 is connected the chair frame 20, which in turn carries the seat 22 and back 24 of the wheelchair 10. The frame 20 additionally includes a pair of handles 26, enabling the wheelchair 10 to be pushed from behind.

Figure 2:
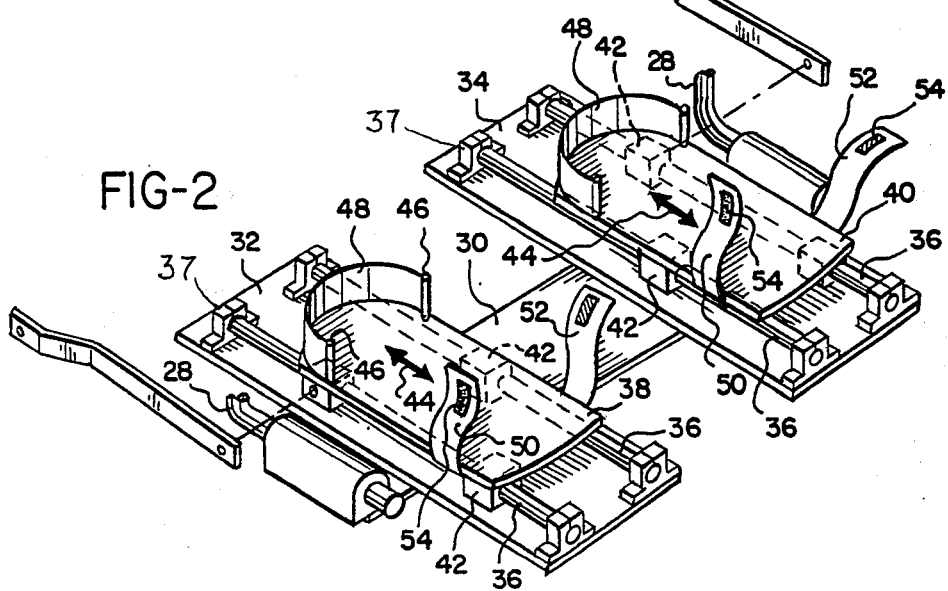
FIG. 2 is a perspective view showing in greater detail the footrests of the wheelchair.

The chair frame 20 further includes a pair of members 28 that extend forwardly from the wheelchair 10 and carry at the ends thereof a foot support platform 30. As seen in FIG. 2, a pair of support plates 32 and 34 are attached to the platform 30, with each including a pair of rods 36 mounted in parallel along the length of plates 32 and 34. Rods 36 are each held in place by a pair of mounting blocks 37, so that a clearance is provided between rods 36 and plates 32 and 34. A pair of footrests 38 and 40 each have three linear ball bearing assemblies 42 mounted to the bottoms thereof, arranged with two of the bearing assemblies 42 toward one side and one toward the other side of each of the footrests 38 and 40. The bearing assemblies 42 in turn ride upon the rods 36 mounted to plates 32 and 34, so that footrests 38 and 40 are carried by plates 32 and 34, respectively, and may be moved therealong in a back and forth manner as indicated by arrows 44.

Each footrest 38 and 40 includes a pair of upwardly projecting posts 46 mounted near the rear end thereof. A flexible heel strip 48 is connected between posts 46, preferably constructed of a material such as nylon webbing, canvas or the like. Each footrest 38 and 40 further includes a pair of toe straps 50 and 52, constructed of the same material as heel straps 48, mounted near the forward end of each footrest. A fastening means, preferably a cooperating pair of hook and loop fastening fabric strips is included for fastening the ends of toe straps 50 and 52.

Figure 3:
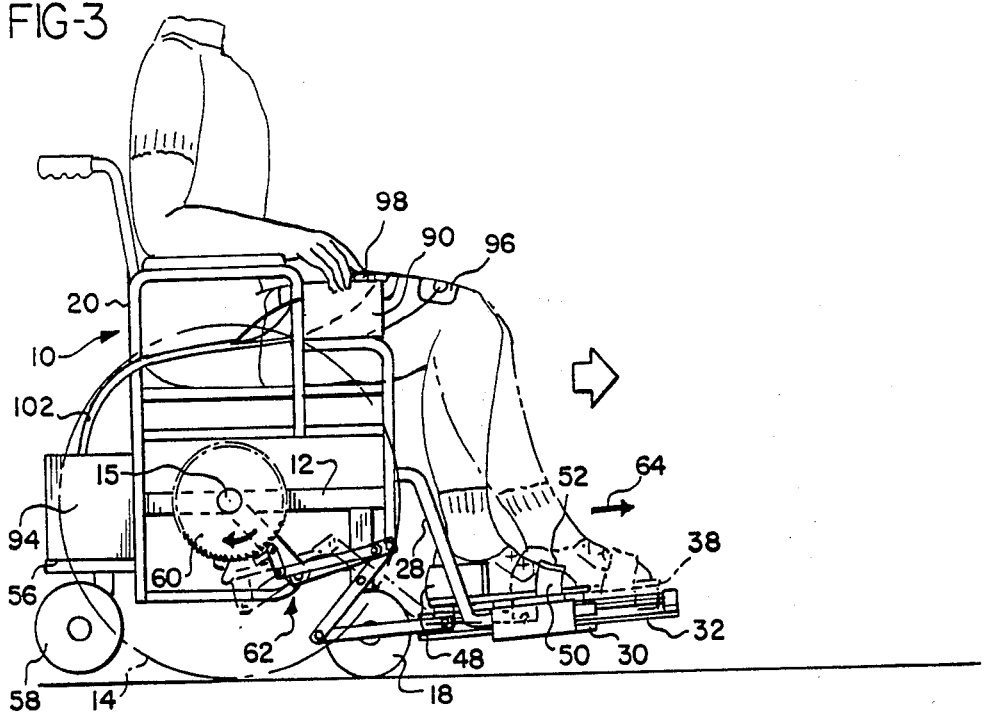
FIG. 3 is an elevational view showing generally the operation of the wheelchair.

The placement of a foot of the occupant of the wheelchair 10 on footrest 38 may be seen by reference to FIG. 3. The heel is placed into the curvature of heel strap 48, and the toe straps 50 and 52 are fastened over the toes of the foot. Of course, it will be recognized that placement of the other foot of the chair occupant upon footrest 40 is identical.

In addition, from FIG. 3 it will be noted that the mounting of footrest 38, and thus of footrest 40 as well, is such that the footrests define a slight angle with respect to the ground so that the travel path of the footrests slope upwardly away from the wheelchair 10. The slope is provided to accommodate the upward movement path of the foot as the lower leg is extended, as well as to facilitate operation of the wheelchair 10 by the leg muscles, as will be described below.

The wheelchair 10 further includes a frame portion 56 extending rearwardly from the main section of frame 20. A rear wheel 58 is attached to frame portion 56, but as can be seen from FIG. 3, wheel 58 is normally not in contact with the ground. Wheel 58 is provided so as to serve as a safety stop in the event wheel chair 10 should fall backwards.

Figure 4:
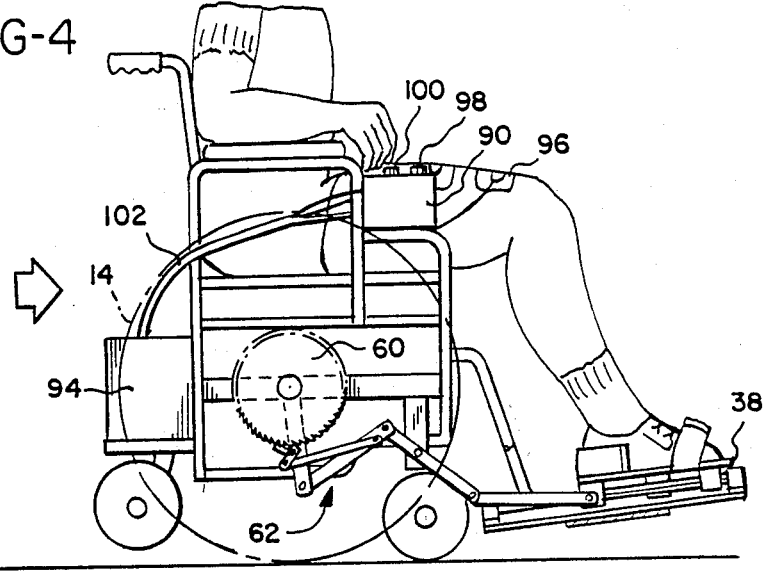
FIG. 4 is a view similar to FIG. 3 showing further the operation of the wheelchair.

The operation of the wheelchair 10 for propulsion by the legs of the chair occupant may be seen generally in FIGS. 3 and 4. A pair of drive gears 60 (only one shown) are mounted adjacent each wheel 14, attached to the same axles 15 supporting the wheels. Each gear 60 rotates in conjunction with the associated wheel 14. A drive means 62, described in greater detail below, is connected between each of the footrests 38 and 40 and a corresponding one of the drive gears 60. To propel the wheelchair 10, one or both of the legs of the chair occupant is extended as shown by arrow 64. The drive means 62 then operates to translate the linear motion of the footrest 38 or 40 into rotary movement for driving the gear 60, and in turn drives the wheelchair 10. Once the leg is extended to the degree remitted by footrest 38 or 40, as seen in FIG. 4, it may be retracted, during which time the drive means 62 becomes disengaged from the gear 60 and returns to its starting position.

The details of the construction and operation of the drive means 62 may be seen by reference to FIGS. 5 and 6. A lever 66 is mounted to the axle 15 supporting driving gear 60 (as well as side wheel 14), but is mounted for pivotal rotation independent from rotation of gear 60 and wheel 14. An arm 68 is pivotally mounted near the center thereof to a depending projection 70 of chassis 12. Pivotally connected to one end of arm 68 is a rod 72. The other end of rod 72 is pivotally mounted to the rearward-most bearing assembly 42 on footrest 38, so that movement of footrest 38 also moves rod 72. A second rod 74 is pivotally connected between the other end of arm 68 and the outermost end of lever 66.

A pawl 76 is pivotally mounted to lever 66 near the outer edge of driving gear 60 for engagement of pawl 76 with gear 60. Pawl 76 is attached by a bolt 78 or the like, which also pivotally connects a linkage 80 to lever 66. As seen in FIG. 7, a spacer 82 is placed on bolt 78 between lever 66 and pawl 76, and a friction pad 84 is disposed on bolt 78 between pawl 76 and linkage 80. Linkage 80 is further pivotally attached to one end of a third rod 86, the other end of rod 86 being pivotally attached to rod 74.

For operation, the drive means 62 is initially positioned as shown in FIG. 5. Extension of the lower leg results in movement of footrest 38 as indicated by arrow 88 in FIG. 6, which carries rod 72 in the same direction. Movement of rod 72 results in pivotal motion of arm 68, whereby rod 74 is moved linearly in a direction opposite that of rod 72. In turn, lever 66 is rotated in a driving direction about driving gear 60.

Lateral movement of rod 74 causes similar movement of rod 86, which rotates linkage 80 about bolt 78. The rotary motion of linkage 80 is transmitted to pawl 76 through friction pad 84, causing pawl 76 to engage the teeth of driving gear 60. Thus, the rotary motion of lever 66 about its axle 15 rotates gear 60, which in turn rotates side wheel 14, driving the wheelchair 10 forward.

Upon complete extension of the leg to the degree permitted by footrest 38, drive means 62 is halted in the position indicated in FIG. 6. Cessation of linear motion of rod 86 and rotational motion of linkage 80 about bolt 78 results in removal of the driving force from pawl 76, which thus drops from engagement with driving gear 60 to a disengaged position where it is held in place by friction pad 84. Movement of the footrest 38 is then begun in the opposite direction, which may be performed solely by gravity due to the slight slope of the footrest assembly, or may be assisted by flexion of the leg muscles. In any event, return motion of footrest 38 causes rod 72 to pivot arm 68 in the opposite direction, whereby rod 74 rotates lever 66 about axle 15 also in the opposite direction.

Since pawl 76 is not longer engaged, rotation of lever 66 has no effect upon driving gear 60, and the wheel chair 10 is not moved in any direction. Once the footrest 38 is returned to its original position, the drive means 62 is again ready for driving of wheelchair 10.

It will, of course, be recognized that a mirror-image drive means 62 is mounted to the wheelchair 10 on its other side, connecting the footrest 40 with the other driving gear 60 and side wheel 14, and operating in a manner indentical to that described above.

Since each side wheel 14 may be rotated freely at all times except during the driving movement of the associated footrest 38 or 40, due to the disengagement of the pawls 76 from gears 60, the wheelchair 10 may be operated in a number of different ways. It can be propelled entirely by the legs of the wheelchair occupant, in which case the occupant's legs may be extended and retracted either in alternating fashion or simultaneously. The wheelchair 10 may be moved by a combination of use of the occupant's arms and legs. Additionally, the wheelchair can be pushed from behind by a second person.

Figure 8:
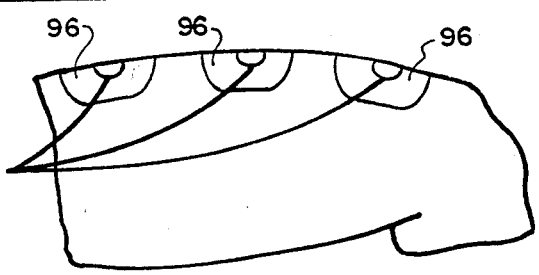
FIG. 8 is an elevational view showing placement of electrodes upon the leg of a chair occupant for stimulation.

The whelchair 10 is propelled by the legs of a paralyzed person through electrical stimulation of the leg muscles. As seen in FIG. 1, the wheelchair 10 includes a control box 90 mounted near one arm 92 of the wheelchair 10. The control box 90 is electrically connected to a stimulator 94, which provides electrical pulses to a series of electrodes 96, which are attached to the occupant's skin adjacent the muscles to be stimulated, namely, the quadriceps muscles of the legs. Electrodes 96 are commercially available transcutaneous electrodes such as MEDTRONIC Model 3793 electrodes sold by Medtronic, Inc. Of Minneapolis, Minn. As shown in FIG. 8, three electrodes 96 are preferably attached to each leg, although any number of electrodes sufficient to provide adequate stimulation may be used. The electrodes 96 are attached to the legs by hypoallergenic tape or elastic bandages. Prior to application of the electrodes 96, the skin is cleaned and dried. An electrode gel, such as TENS electrode gel, also sold by Medtronic, Inc., is applied to the electrodes 96 before they are placed upon the skin of the chair occupant.

In one embodiment of the invention, the stimulator 94 may be a solid-state square pulse stimulator, such as a GRASS Model SD 9, manufactured by Grass Instrument Company of Quincy, Mass. The stimulator is used for simple ON/OFF stimulation of the quadriceps muscles, controlled by a pair of push button switches 98 and 100 included in the control box 90. A multi-wire cable 102, shown in FIGS. 3 and 4, is used to convey wires from both control box 90 and the electrodes 96 to the stimulator 94, which is mounted at the rear of wheelchair 10 to frame portion 56 along with the necessary battery (not shown) for supplying power to stimulator 94.

Operation of the stimulation apparatus is commenced by depressing push button 98 of control box 90, as shown in FIG. 3. Stimulator 94 in response provides an output stimulation signal to the electrodes 96 attached to the right leg. The right quadriceps contracts whereby the lower leg and foot is extended outwardly, causing forward driving of the wheelchair 10 as has been described herein. Upon observing that the leg is fully extended, as shown in FIG. 4, the occupant of the chair releases pushbutton 98, whereupon stimulation of the quadriceps ceases. It will be recalled that the drive means 62 will now disengage from driving gear 60. Due to the slight incline of footrest 38, the right foot is then returned by gravity to its starting position. The occupant then depresses the second pushbutton 100, causing stimulation of the left quadriceps in a manner identical to that described for the right. Pushbutton 100 is released after full extension of the left lower leg, whereupon it is returned by gravity to its starting position.

Of course, it will be recognized that a number of other forms of apparatus for providing electrical stimulation for driving the wheelchair 10 may be used. A more complex and preferred apparatus uses a particular stimulator, which will be described below in conjunction with a second species of vehicle. Details of the adaptation of the stimulator for use with the wheelchair 10 will also be described below.

Figure 9:
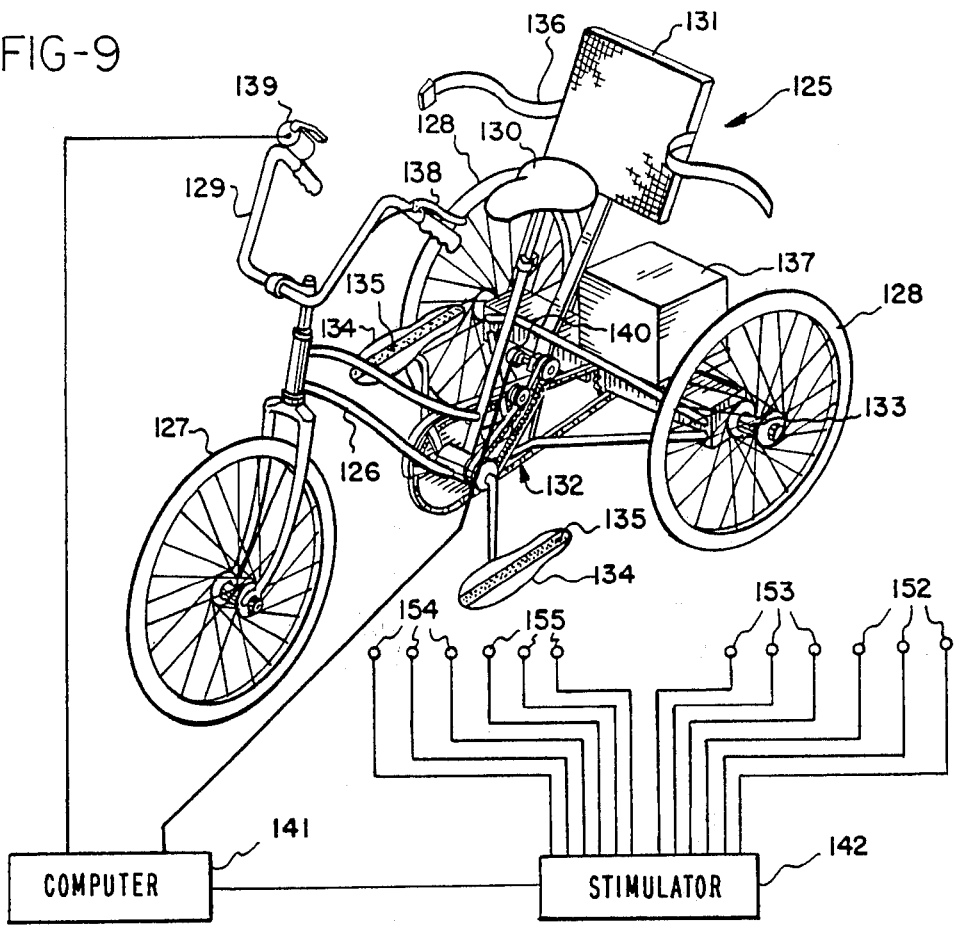
FIG. 9 is a perspective view showing a tricycle as a second embodiment of the present invention, along with a schematic representation of a circuit for providing electrical stimulation to the legs of a paralyzed tricycle rider.

A second species of vehicle in accordance with this invention is illustrated generally in FIG. 9. The vehicle as shown is a modified version of a commercially available tricycle. Thus the vehicle 125 comprises a frame 126, a front wheel 127, a pair of rear wheels 127, 128, handlebars 129, and a seat 130. A backrest 131 is welded to frame 126 for supporting a paralyzed person seated on seat 130. A safety strap 136 is also provided. For operation of tricycle 125, as described herein, the rider should have at least some limited use of his hands.

Figure 11:
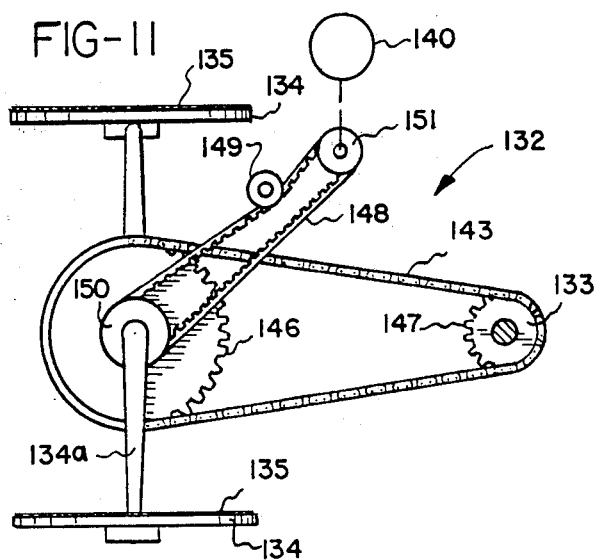
FIG. 11 is an elevational view showing in detail the drive system of the tricycle.

A pair of pedals 134, 134 mounted to crank 134a are provided to power a chain drive 132 in the normal manner. Chain drive 132 is connected to rear axle 133 as best illustrated in FIG. 11. Thus pedals 134, 134 rotate a driving sprocket 146 which drives a chain 143 for rotation of a driven sprocket 147. A conventional hand brake 138 is also provided.

In order to enable operation of tricycle 125 by a paralyzed person, the system includes a stimulator 142 and electrode sets 152, 153, 154 and 155, the operation of which will be described below. Stimulator 142 is controlled by a computer 141, which reacts to a speed control signal from a speed controller 139 and a pedal position signal from a pedal position sensor 140. Computer 141 and stimulator 142, together with their associated power supplies are mounted within a box 137 carried at the rear of the tricycle. The feet of the rider are maintained in contact with pedals 134 by means of a pair of fabric strips 135, 135. Fabric strips 135, 135 are hook and loop fastening fabric which grips similar fabric applied to the soles of the shoes worn by the rider.

Figure 10:
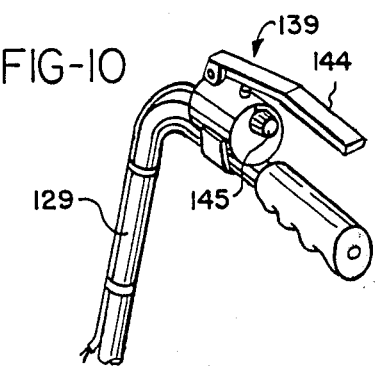
FIG. 10 is a perspective view of a portion of the handlebars of the tricycle, showing the speed controller.

As best shown in FIG. 10, speed controller 139 includes a speed control dial 145 and a switch handle 144. The rider controls the speed by adjusting the speed dial 145 to the desired position and then gripping switch handle 144. Switch handle 144 operates a switch 234 which is attached to a spring 237 in such a manner as to prevent the generation of any muscle stimulation signals unless switch handle 144 is being gripped.

As shown in FIG. 11 pedal sensor 140 is connected for rotation by a driven roller 151. Driven roller 151 is driven by a toothed belt 148, which in turn wraps around a drive roller 150. Drive roller 150 is rotated by rotation of pedals 134, 134.

Figure 12:
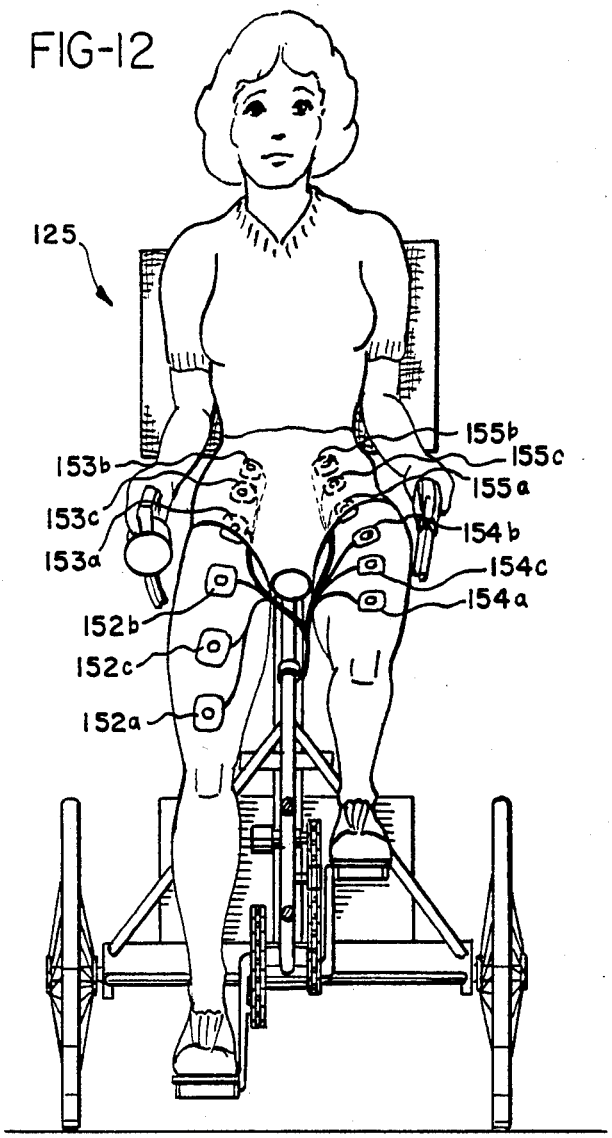
FIG. 12 is an elevational front view, with a portion of the tricycle broken away, showing positioning of the electrodes on the tricycle rider.

As illustrated in FIG. 12, stimulation electrodes 152 are applied to the right leg of the rider immediately above the quadraceps muscles for controlling the position of the lower right leg. Electrodes 152, are designated in FIG. 12 as electrodes 152a, 152c and 152b in order to emphasize the different electrical connection for each electrode. These electrodes are of the same type as electrodes 96, which were described above. Also of the same construction are electrodes 154a, 154c and 154b, which produce movement of the left lower leg and which are positioned above the left quadraceps muscles.

The system also includes a set of somewhat smaller electrodes 153a, 153c and 153b which are positioned above the right illiac muscle and electrodes 155a, 155c and 155b which are positioned above the left illiac muscle. Electrodes 153 and 155 produce lifting movement of the upper right and left legs respectively. These latter electrodes may be MEDTRONIC models 3795 electrodes.

Figure 15:
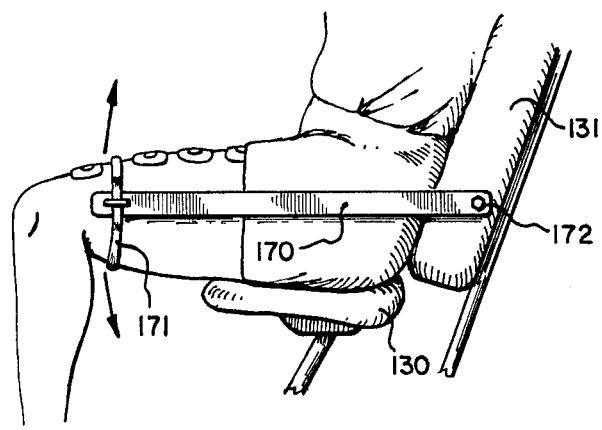
FIG. 15 is an elevational view illustrating a hip support brace for assisting the rider in operating the tricycle.

FIG. 15 illustrates a hip support brace which may be used to assist the rider in operating the above described tricycle. Braces of this general type may be used to keep the legs from moving sidewardly in and out. For the normal healthy individual slight muscle activity keeps the hips from moving in and out during forward pedaling. However, in the paralyzed person, this is impossible. Therefore support means should be provided. A satisfactory brace, such as the illustrated brace 170 may be of single piece construction and may be secured to backrest 131 at a pivot point 172, which permits up and down rotation only. Hip support brace 170 may be secured to the leg of the rider by any suitable strap 171. Another hip support brace (not illustrated) is similarly strapped to the other leg.

Figure 13:
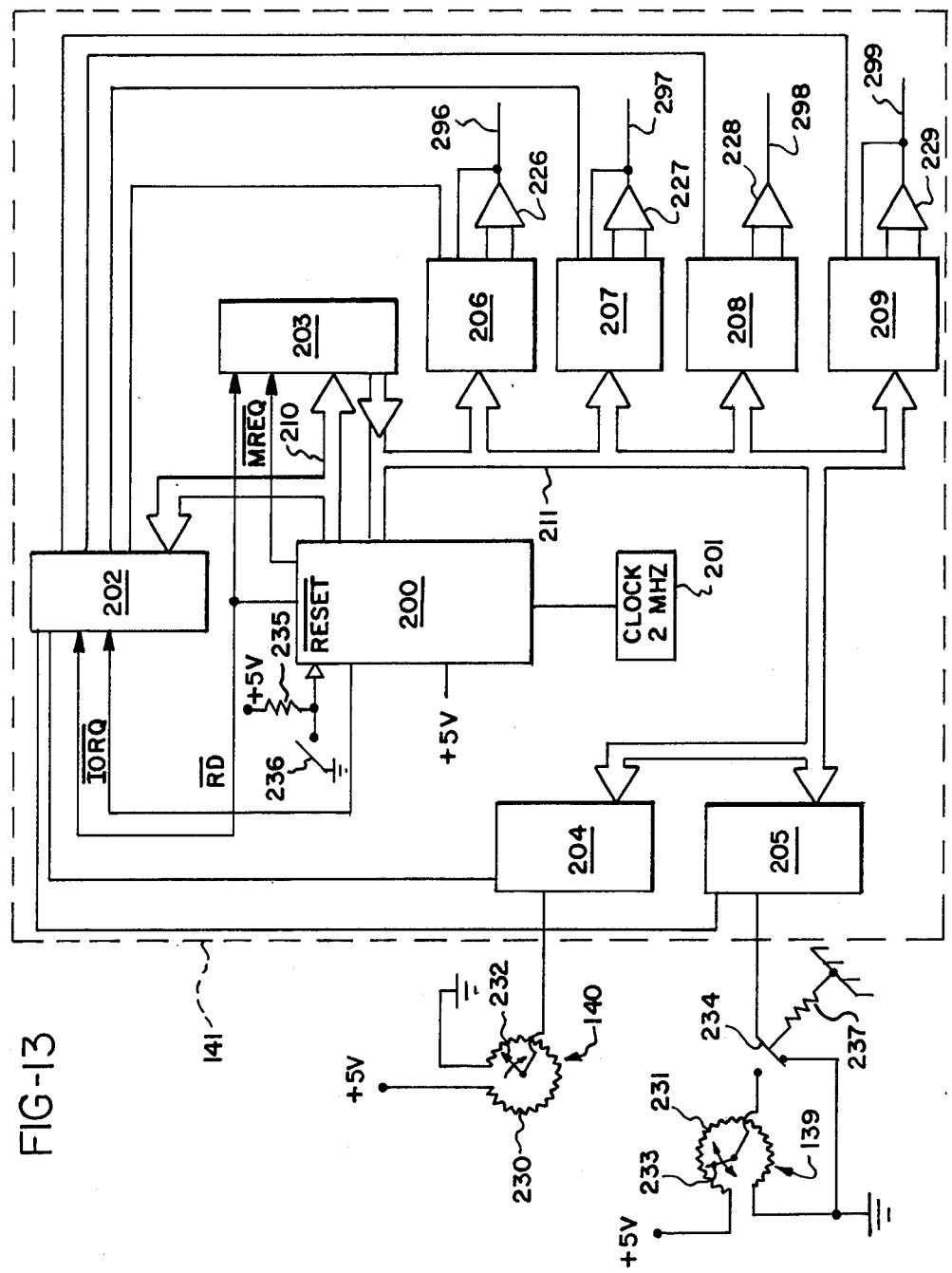
FIG. 13 is a schematic illustration of the computer.

As illustrated in FIG. 13, computer 141 comprises a Z80 microprocessor a 200 MHz clock 201, a decoder/demultiplexer 202, a 2000 word EPROM memory 203, two analog/digital converters 204, 205, and four digital/analog converters 206 through 209. Tables I and II summarize the integrated circuits and the components employed by the system, including computer 141 and stimulator 142.

TABLE I

| Ref. Numeral | Integrated Circuits Circuit Type |
| --- | --- |
| 200 | Z80 (Zilog) |
| 202 | SN74LS138 (Texas Instrument) |
| 203 | 2716 (Hitachi) |
| 204 | AD 7574 (Analog Devices) |
| 205 | AD 7574 (Analog Devices) |
| 206 | DAC0832 (National Semiconductor) |
| 207 | DAC0832 (National Semiconductor) |
| 208 | DAC0832 (National Semiconductor) |
| 209 | DAC0832 (National Semiconductor) |
| 226 | ¼ LM1458 |
| 227 | ¼ LM1458 |
| 228 | ¼ LM1458 |
| 229 | ¼ LM1458 |

TABLE II

| Ref. Numeral | Components Identification |
| --- | --- |
| 230 | 20k |
| 231 | 50k |
| 235 | 1k |
| 304 | 2N3904 |
| 305 | 2N3904 |
| 306 | 2N3904 |
| 307 | 2N3904 |
| 308 | 2N3904 |
| 311 | 2SC1308 |
| 312 | 2SC1308 |
| 313 | 100k |
| 314 | 100k |
| 315 | 0.1 μf |
| 326 | 10k |
| 317 | 0.1 μf |
| 318 | 10k |
| 319 | 10k |
| 320 | 0.001 μf |
| 321 | 22k |
| 322 | 0.001 μf |
| 323 | 22k |
| 324 | 10k |
| 325 | 0.1 μf |
| 326 | 470Ω |
| 327 | 10k |
| 328 | 470Ω |
| 329 | 470Ω |
| 330 | 10k |
| 331 | 470Ω |
| 332 | 1k |
| 333 | 1k |
| 334 | 100Ω |
| 335 | 100Ω |
| 336 | 0.1 μf |

The program for controlling the operation of computer 141 is permanently stored in EPROM 203, and a typical program listing is set forth in Table III. EPROM 203 is addressed by address lines $A_0$ to $A_{10}$ of the system address bus 210. The system address bus includes five additional lines which are not required for the practice of the invention as described herein. Two address lines, $A_0$ and $A_1$ are also connected for addressing decoder/demultiplexer 202. Microprocessor 200 is connected for addressing either decoder/demultiplexer 202 or EPROM 203 in the manner well known in the art.

Computer 141 also comprises a data bus 211, which interconnects microprocessor 200 with EPROM 203, A/D converters 204 and 205, and D/A converters 206 to 209. When microprocessor 200 addresses memory 203, the memory responds by transmitting eight-bit instruction codes on data bus 211. These instructions control the operation of the computer, including the generation of addresses and the reading and writing of data. Microprocessor 200 may be reset by a switch 236 connected to the $\overline{RESET}$ terminal thereof.

Computer 141 has six output ports with ports 0 through 3 being associated respectively with D/A converters 206 through 209 and ports 4 and 5 being associated respectively with A/D converters 204 and 205. Selection of input/output ports for reading or writing is carried out through decoder/demultiplexer 202. Decoder/demultiplexer 202 selects the ports by decoding the $\overline{IORQ}$ output from microprocessor 200 and the lower two address bits of the address bus.

When the computer desires to read the pedal position, IC 202 is addressed for seletion of A/D converter 204. A/D converter 204 then reads an analog signal representing pedal position, digitizes that signal and transmits the digital representation thereof along data bus 211 to microprocessor 200. Similarly, IC 202 selects A/D converter 205 for reading and digitizing speed control commands. Thereafter IC 202 selects D/A converters 206 through 209 for reception of signals on the data bus representing muscle stimulation commands. Each of D/A converters 206 through 209 has an associated operational amplifier 226 through 229 respectively for providing analog stimulation commands having a potential ranging between 0 and 10 volts.

Speed control 139 comprises a 50K circular resistor connected for operation as a rotary potentiometer. Accordingly resistor 231 is connected to a five volt power supply and is contacted by a wiper contact 233. Normally open switch 234 prevents generation of a speed control signal, except when the handle 144 is being manually depressed. When switch 234 is closed a speed control signal representing a desired speed is supplied to A/D converter 205. A/D converter 205 digitizes the speed control signal and transmits it upon command to data bus 211.

Pedal sensor 140 comprises a 20K circular resistor, also connected for operation as a rotary potentiometer. Accordingly resistor 230 is connected to a five volt power supply and is contacted by a wiper arm 230. Output signals from pedal sensors 140 are applied to A/D converter 204 for digitizing and transmission to microprocessor 200 along data bus 211.

Wiper arm 232 rotates one time for each rotation of pedals 134 while concomitantly generating an ouput signal varying from 0 to 5 volts. The pedals are set up in such a manner that sensor 140 has a 0 volt output when the right leg is at the very top of its rotational arc. This is defined as top dead center.

Figure 14:
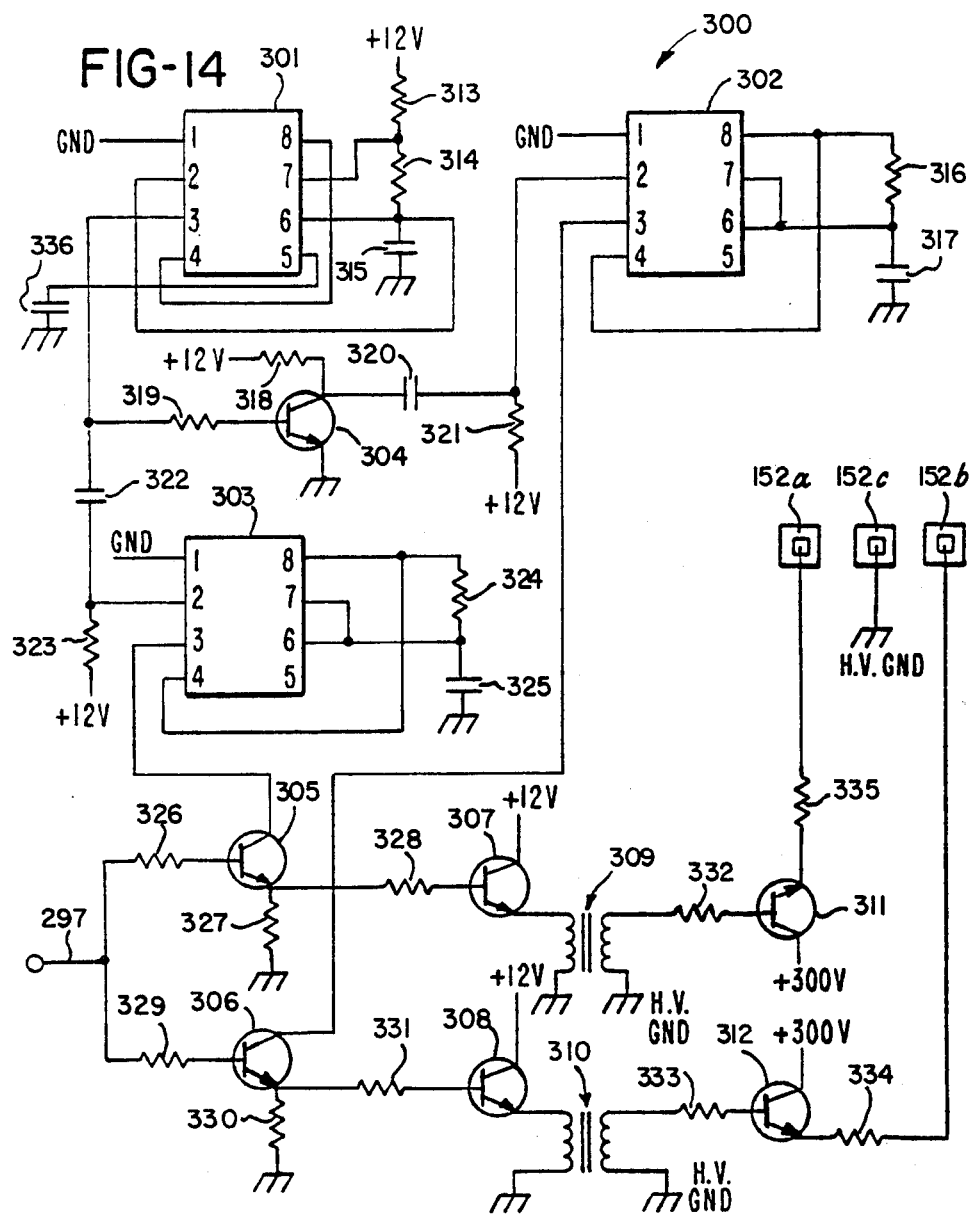
FIG. 14 is a schematic illustration of the stimulator.

The stimulator control system for operation of the tricycle 125 includes four separate but similar channels connected for operation under the control of analog signals generated by D/A converters 206 through 209. These analog signals appear at output lines 296 through 299 respectively. The construction of one such channel will now be described with reference to FIG. 14. That channel is designated by the reference numeral 300 and comprises one-fourth of stimulator 142.

Stimulation channel 300 receives its control signal on line 297 and generates stimulation voltages for electrodes 152a, 152c and 152b. As mentioned above, these electrodes produce stimulation of the right quadraceps muscles. Stimulation channel 300 includes three integrated circuits 301, 302 and 303 of identical construction. These are timing circuits such as Signetics 555 timers. IC 301 is connected to operate as a 60 Hz free running multivibrator.

The output from IC 301 is applied via transistor 304 to input pins 2 of IC 302 and 303. IC 302 and 303 produce alternating 500 microsecond pulses, each at a frequency of 60 Hz, for application to the collector terminals of transistors 305 and 306. The pulse width is set by appropriate selection of the resistance of resistors 316 and 324 and the capacitance of capacitors 317 and 325, as shown in the manufacturer's data sheets for integrated circuits 302 and 303. The phase between the pulses produced by integrated circuits 302 and 303 is set by appropriate selection of the resistance for resistors 313 and 314.

The analog voltage representing the desired amplitude for the stimulation pulses is applied to line 297, as mentioned above. The analog input is supplied to the base terminals of transistors 305 and 306. Concomitantly, output pulses from pin 3 of IC 302 and pin 3 of IC 303 are applied to the collectors of transistors 306 and 305 respectively. As a result thereof transistors 306 and 305 generate emitter currents across resistors 330 and 327 providing voltage pulses of appropriate phase and duration for muscle stimulation. These voltages are applied to the base terminals of transistors 308 and 307. The pulses are thereby amplified and applied to the primary winding of transformers 310 and 309. At this point the pulses have amplitudes ranging between 0 and 12 volts.

The voltage pulses across the primary windings of transformers 310 and 309 produce low current high voltage pulses ranging from 0 to 255 volts across the secondary windings of transformers 310 and 309. The secondary windings of transformers 310 and 309 have one side grounded to a high voltage ground which is different from the ground utilized for the primary windings thereof. The output pulses from the secondary windings are thereby RF isolated to maintain the safety of the person who is riding the tricycle.

Figure 16:
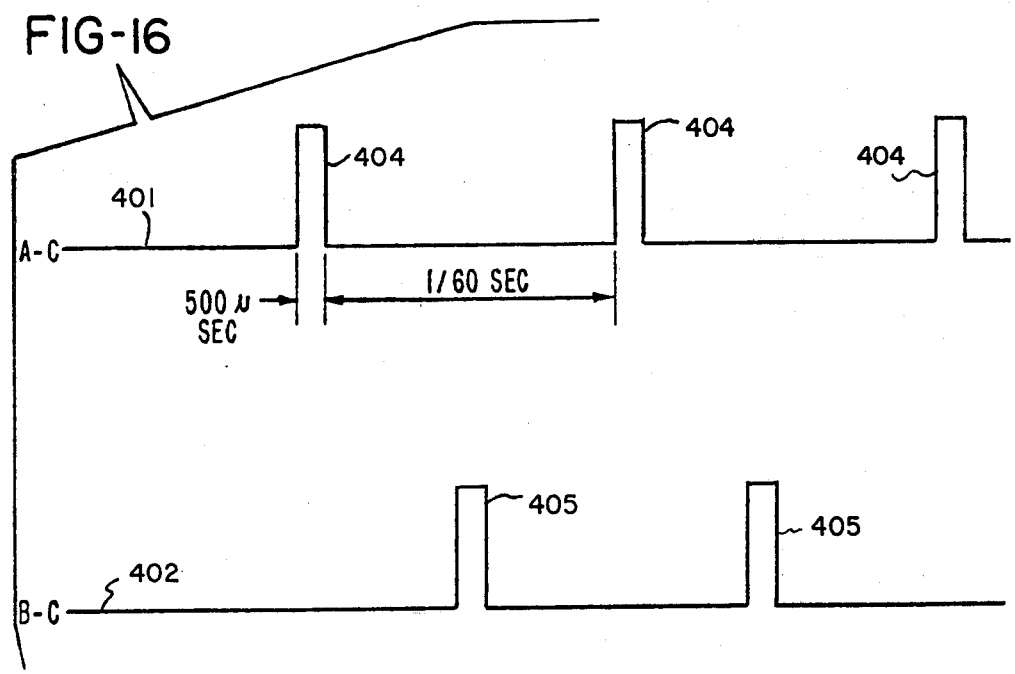
FIG. 16 is a schematic illustration of a stimulation signal.

Output voltage pulses from transformers 310 and 309 are applied to the base terminals of transistors 312 and 311 respectively. Transistors 312 and 311 provide a current gain so as to have high current, high voltage and low duty cycle pulses available for application across terminal pairs 152a-152c and 152b-152c. The output signal profiles appear as generally illustrated in FIG. 16. Thus the signal across terminals 152a-152c appears as illustrated by the line 401, while the signal across terminals 152b-152c appears as illustrated by the line 402. Signal 401 comprises pulses of 500 microseconds duration occurring at a frequency of 60 Hz. These pulses 404 alternate in time with pulses 405 of signal 402. The amplitude of the pulses is controlled by speed controller 139 through computer 141.

Stimulation signals to electrode sets 152, 153, 154 and 155 are gated on and off under control of pedal position signals from pedal sensor 140. As mentioned above, position angles are measured with reference to the point when the right pedal is at top dead center. If the legs are within the first 90° of rotation, then the right quadriceps muscles are stimulated. At the same time the left illiac is stimulated to lift the leg up. During the next 90° of rotation the right quadriceps are turned off and the left illiac remains stimulated. From 180° to 270° of rotation the left quadriceps are turned on as well as the right illiac. This enables the left leg to go down and the right leg to be lifted. During the final 90° of rotation, the left quadriceps are turned off and the right illiac continue to be stimulated. This completes the stimulation cycle.

Following completion of a stimulation cycle throttle sensor 139 is sampled and the rotation is repeated. As a consequence of the stimulation cycle, the right leg pushes down on the right pedal while the left leg is lifted. This is followed by pushing down of the left leg and lifting of the right leg. The details of the stimulation sequence can be understood by reference to the program listing of Table III.

TABLE III

| Bicycle Program Listing for Z80 Microprocessor | | |
|---|---|---|
| 1: | | |
| 2: | | |
| 3: | 8000 | ORG 8000H |
| 4: | 8000 3E00 | MVI A,00 |
| 5: | 8002 D301 | OUT 1 |
| 6: | 8004 D302 | OUT 2 |
| 7: | 8006 D303 | OUT 3 |

TABLE III-continued

Bicycle
Program Listing for Z80 Microprocessor

| | | | |
|---|---|---|---|
| 8: | 8008 D300 | OUT 0 | |
| 9: | 800A 3E00 | AGAIN MVI A,00 | |
| 10: | 800C C601 | RR ADI 01 | |
| 11: | 800E C20C80 | JNZ RR | |
| 12: | 8011 DB04 | IN 04 | |
| 13: | 8013 3EF0 | MVI A,240 | |
| 14: | 8015 C601 | LOOP ADI 01 | |
| 15: | 8017 C21580 | JNZ LOOP; A/D DELAY | |
| 16: | 801A 5F | MOV E,A | |
| 17: | 801B DB04 | IN 04 | |
| 18: | 801D E67F | ANI 7FH | |
| 19: | 801F FE19 | CPI 25 | |
| 20: | 8021 FA0000 | JM 0000 | |
| 21: | 8024 5F | MOV E,A | |
| 22: | 8025 DB05 | IN 05 | |
| 23: | 8027 3EF0 | MVI A,240 | |
| 24: | 8029 C801 | HH ADI 01 | |
| 25: | 802B C22980 | JNZ HH | |
| 26: | 802E DB05 | IN 05 | |
| 27: | 8030 E67F | ANI 7FH | |
| 28: | 8032 E67F | ANI 7FH | |
| 29: | 8034 6F | MOV L,A | |
| 0: | 8035 FE07 | CPI 07H | |
| 31: | 8037 FA0000 | JM 0000 | |
| 32: | 803A FE24 | CPI 36 | |
| 33: | 803C FA0001 | JM 0100H | |
| 34: | 803F FE46 | CPI 70 | |
| 35: | 8041 FA0002 | JM 0200H | |
| 36: | 8044 FE65 | CPI 101 | |
| 37: | 8046 FA0003 | JM 0300H | |
| 38: | 8049 FE7D | CPI 125 | |
| 39: | 804B FA0004 | JM 0400H | |
| 40: | 804E C30000 | JMP 0000 | |
| 41: | | ; SUBROUTINES | |
| 42: | | ; | |
| 43: | | ; | |
| 44: | | ; | |
| 45: | | | |
| 46: | 8100 | ORG 8100H | |
| 47: | | ; SYSTEM REQUIRES 1=RGAS 2=LGAS 3=RIL 4=LIL | |
| 48: | | ; | |
| 49: | | ; | |
| 50: | 8100 7B | MOV A,E | |
| 51: | 8101 D300 | OUT 0 | |
| 52: | 8103 3E4B | MVI A,75 | |
| 53: | 8105 D303 | OUT 3 | |
| 54: | 8107 3E00 | MVI A,00 | |
| 55: | 8109 D301 | OUT 1 | |
| 56: | 810B D302 | OUT 2 | |
| 57: | 810D C30A80 | JMP AGAIN | |
| 58: | | ; | |
| 59: | 8200 | ORG 8200H | |
| 60: | 8200 00 | NOP;90 DEGREE IN ROUTINE | |
| 61: | 8201 3E00 | MVI A,0 | |
| 62: | 8203 D300 | OUT 0 | |
| 63: | 8205 D301 | OUT 1 | |
| 64: | 8207 D302 | OUT 2 | |
| 65: | 8209 3E41 | MVI A,65 | |
| 66: | 820B D303 | OUT 3 | |
| 67: | 820D 030A80 | JMP AGAIN; START OVER | |
| 68: | | ; | |
| 69: | | | |
| 70: | 8300 | ORG 8300H | |
| 71: | 8300 7B | MOV A,E | |
| 72: | 8301 D301 | OUT 1 | |
| 73: | 8303 3E00 | MVI A,00 | |
| 74: | 8305 D300 | OUT 0 | |
| 75: | 8307 D303 | OUT 3 | |
| 76: | 8309 3E4B | MVI A,75 | |
| 77: | 830B D302 | OUT 2 | |
| 78: | 830D C30A80 | JMP AGAIN | |
| 79: | | ; | |
| 80: | | ; | |
| 81: | | ; | |
| 82: | | ; | |
| 83: | 8400 | ORG 8400H | |
| 84: | 8400 3E00 | MVI A,00 | |
| 85: | 8402 D300 | OUT 0 | |
| 86: | 8404 D301 | OUT 1 | |
| 87: | 8406 D303 | OUT 3 | |
| 88: | 8408 3E41 | MVI A,65 | |
| 89: | 840A D302 | OUT 2 | |
| 90: | 840C C30A80 | JMP AGAIN | |

As was noted above, the stimulation circuit as has been disclosed may be used to provide electrical stimulation to the legs of an occupant of the wheelchair 10. In such an embodiment, a pair of stimulation channels 300 are used, one for each of the sets of electrodes 96 attached to each of the legs of the chair occupant. Push buttons 98 and 100 supply ON/OFF analog control voltages to line 297 of each stimulation channel 300. Each channel 300 in turn supplies a pair of alternatingly pulsed stimulation signals to one of the sets of three electrodes 96 placed on one of the legs of the occupant as illustrated in FIG. 8. For such operation, the center electrode 96 of each set is connected to high voltage ground, while the two outside electrodes are active.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. A vehicle for transporting a paralyzed person comprising:
   a support frame for carrying said person;
   a plurality of wheels for carrying said support frame;
   limb support means connected to said support frame for supporting a limb of said person;
   drive means connected between said limb support means and at least one of said wheels for driving said vehicle in response to movement of said limb;
   control means for generating a control signal; and
   stimulation means responsive to said control signal for stimulating a muscle of said person to cause driving movement of said limb.

2. A vehicle as defined in claim 1, wherein said limb support means comprises means for supporting the feet of said person, said feet supporting means being movable in response to driving movement of the legs of said person.

3. A vehicle for transporting a paralyzed person comprising:
   a support frame for carrying said person;
   a plurality of wheels for carrying said support frame;
   feet support means movably connected to said support frame for supporting the feet of said person;
   drive means connected between said feet support means and at least one of said wheels for driving said vehicle in response to movement of the legs of said person;
   means for generating a plurality of stimulation signals;
   stimulation means responsive to said stimulation signals for causing driving movement of said legs; and
   control means for selectively actuating said stimulation signal generating means.

4. A vehicle as defined in claim 3, wherein said stimulation means includes a plurality of sets of electrodes constructed for attachment to the skin of said person, at least one of said sets being attached along each of the legs of said person.

5. A vehicle as defined in claim 4, wherein each of said sets of electrodes is responsive to a pair of said stimulation signals.

6. A vehicle as defined in claim 5, wherein each of said stimulation signals comprises pulses which alternate with pulses in another stimulation signal applied to the same set of electrodes.

7. A vehicle as defined in claim 5, wherein said feet support means comprises a pair of pedals for rotational motion by said driving movement of the legs of said person and further wherein said drive means comprises a rotatable crank for opposed mounting of said pedals and for rotational driving in response to rotational motion of said pedals.

8. A vehicle as defined in claim 7, wherein said stimulation means includes at least four of said sets of electrodes, a first of said sets being attached for stimulation of the quadriceps muscle of the right leg of said person, a second of said sets being attached for stimulation of the right illiac muscle of said person, a third of said sets being attached for stimulation of the quadriceps muscle of the left leg of said person, and a fourth of said sets being attached for stimulation of the left illiac muscle of said person.

9. A vehicle as defined in claim 8, further comprising sensing means for generating a position sensing signal corresponding to forward rotation of said crank, said control means being operative in response to said position sensing signal to apply a pair of said stimulation signals to each of said sets of electrodes in a sequence to cause the legs of said person to rotate said crank.

10. A vehicle as defined in claim 9 wherein said control means applies pairs of said stimulation signals simultaneously to said first and fourth sets of electrodes when said position sensing signal indicates that the right foot of said person is between 0° and 90° from a top dead center position, applies a pair of said stimulation signals to said fourth set of electrodes when said right foot is between 90° and 180° from top dead center, applies pairs of said stimulation signals simultaneously to said second and third sets of electrodes when said right foot is between 180° and 270° from top dead center, and applies a pair of said stimulation signals to raise second set of electrodes when said right foot is between 270° and 360° from top dead center.

11. A vehicle as defined in claim 9, further comprising speed selection means, said control means being responsive to said speed selection means for selectively regulating the amplitude of said stimulation signals, thereby regulating the speed of said vehicle.

12. A vehicle according to any of claims 6–11 wherein each of said stimulation signal comprises pulses generated at a frequency of about 60 Hz.

13. A vehicle according to claim 12 wherein said pulses have a duration of about 500 microseconds.

14. A vehicle for transporting a paralyzed person comprising:
a support frame for carrying said person, limb support means connected to said support frame for movably supporting a limb of said person,
stimulator means for stimulating a paralyzed muscle of said person to produce movement of said limb support means,
drive means powered by movement of said limb support means for producing motion of said vehicle,
sensing means for sensing movement produced as a result of said muscle stimulation, and
control means responsive to said sensing means for controlling the operation of said stimulator means.

* * * * *